United States Patent
Luther

(10) Patent No.: US 6,500,157 B2
(45) Date of Patent: *Dec. 31, 2002

(54) INTRAVENOUS INFUSION NEEDLE WITH SOFT BODY

(76) Inventor: Ronald B. Luther, 530 Kings Rd., Newport Beach, CA (US) 92663-5710

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/146,451

(22) Filed: Sep. 3, 1998

(65) Prior Publication Data

US 2001/0044604 A1 Nov. 22, 2001

(51) Int. Cl.7 ................................................ A61M 5/00
(52) U.S. Cl. ...................................... 604/264; 604/272
(58) Field of Search ............................ 604/264, 198, 604/168, 272, 110, 164, 164.06, 164.09

(56) References Cited

U.S. PATENT DOCUMENTS

| | | | | |
|---|---|---|---|---|
| 2,717,599 A | * | 9/1955 | Hubber | 604/274 |
| 3,448,740 A | * | 6/1969 | Figge | 604/274 |
| 3,589,363 A | * | 6/1971 | Banko et al. | 604/22 |
| 3,645,268 A | * | 2/1972 | Capote | 604/117 |
| 3,780,733 A | * | 12/1973 | Martinez-Manzor | 604/158 |
| 4,343,305 A | * | 8/1982 | Bron | 137/501 |
| 4,565,545 A | * | 1/1986 | Suzuki | 604/164 |
| 4,626,240 A | * | 12/1986 | Edelman et al. | 604/43 |
| 4,702,260 A | * | 10/1987 | Wang | 600/564 |
| 4,763,667 A | * | 8/1988 | Manzo | 128/750 |
| 4,767,407 A | * | 8/1988 | Foran | 604/164 |
| 4,781,691 A | * | 11/1988 | Gross | 604/164 |
| 4,795,446 A | * | 1/1989 | Fecht | 604/239 |
| 4,808,156 A | * | 2/1989 | Dean | 604/43 |
| 4,869,717 A | * | 9/1989 | Adair | 604/51 |
| 5,106,376 A | * | 4/1992 | Mononen et al. | 604/158 |
| 5,137,515 A | * | 8/1992 | Hogan | 604/110 |
| 5,295,974 A | * | 3/1994 | O'Laughlin | 604/198 |
| 5,295,980 A | * | 3/1994 | Ersek | 604/272 |
| 5,312,345 A | | 5/1994 | Cole | |
| 5,330,434 A | * | 7/1994 | McFarlane | 604/164 |
| 5,334,185 A | * | 8/1994 | Giesy et al. | 604/164 |
| 5,403,283 A | | 4/1995 | Luther | |
| 5,419,766 A | * | 5/1995 | Chang et al. | 604/110 |
| 5,531,701 A | | 7/1996 | Luther | |
| 5,533,988 A | | 7/1996 | Dickerson et al. | |
| 5,569,217 A | | 10/1996 | Luther | |
| 5,634,913 A | * | 6/1997 | Stinger | 604/272 |
| 5,683,370 A | | 11/1997 | Luther et al. | |
| 5,685,855 A | * | 11/1997 | Erskine | 604/168 |
| 5,913,848 A | | 6/1999 | Luther et al. | |
| 5,916,208 A | | 6/1999 | Luther et al. | |
| 5,935,108 A | * | 8/1999 | Katoh et al. | 604/164 |
| 6,203,533 B1 | * | 3/2001 | Ouchi | 604/264 |
| 6,217,527 B1 | * | 4/2001 | Selmon et al. | 600/585 |

* cited by examiner

Primary Examiner—Brian L. Casler
Assistant Examiner—Kevin C. Sirmons
(74) Attorney, Agent, or Firm—Knobbe, Martens, Olson & Bear, LLP.

(57) ABSTRACT

Disclosed is a catheter having a flexible tube and a sharpened needle secured to the catheter at its distal end. The catheter does not require a separate sharpened instrument to enable insertion into an anatomical passageway. The sharpened needle of the catheter remains disposed within an anatomical passageway during treatment. Also disclosed is a catheter assembly comprising the catheter and a safety inserter. The safety inserter has a blunt end and facilitates the insertion of the catheter by providing a mechanism to urge the sharpened needle of the catheter into an anatomical passageway. Also disclosed is an improved needle tip which minimizes trauma to an anatomical passageway. Also disclosed are methods of using and forming the catheter, catheter assembly and needle tip.

13 Claims, 3 Drawing Sheets

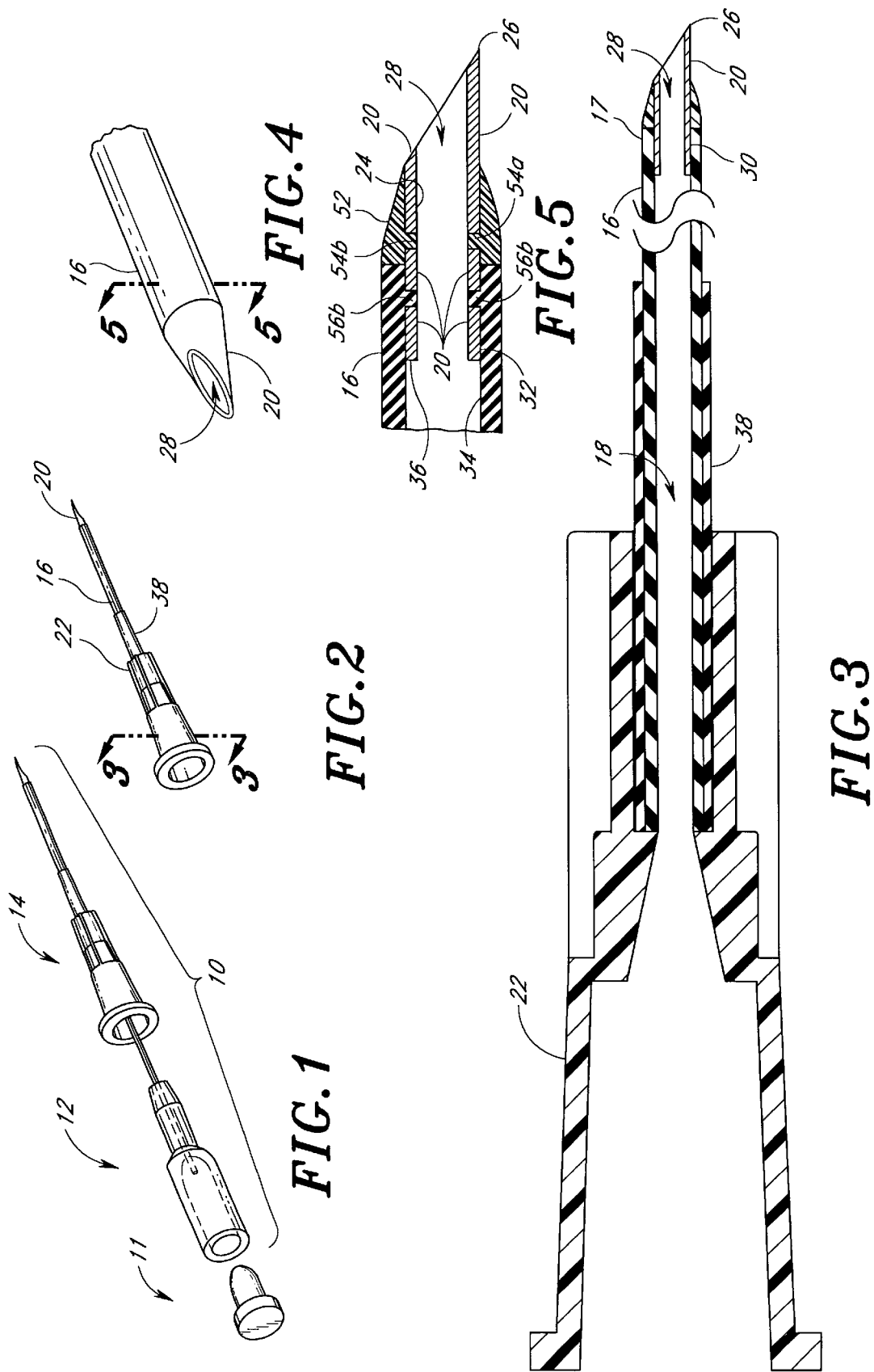

INTRAVENOUS INFUSION NEEDLE WITH SOFT BODY

BACKGROUND OF THE INVENTION

The present invention relates to an improved catheter, and more particularly to an improved catheter which provides an increased viable lifetime and also minimizes potential trauma to the patient and the possibility of accidental needle contact with the medical practitioner.

Catheters are used for introducing fluids into an anatomical passageway of a patient undergoing treatment. Typically, a catheter is inserted into the anatomical passageway, such as a blood vessel. The catheter is then connected to an administration line from which fluids are introduced into the patient's vascular system through the catheter. Alternatively, catheters may be placed directly into tissue of a patient, such as a muscle or organ so that a fluid medication may be administered directly to a specific site asystemically as is well understood by those of skill in the art.

There are various methods of inserting a catheter into an anatomical passageway. These methods typically involve the use of a sharpened metal needle in conjunction with the catheter. In one such method the metal needle defines a lumen. The metal needle is inserted into the patient's anatomical passageway. Once the needle is in place, the catheter is introduced through the lumen and into the passageway. This type of catheter system is known as a through-the-needle system. Once the catheter is inserted, the needle is removed. This requires the medical practitioner to pull the needle with its sharp edge out of the patient and guide it over or along the catheter until it is removed.

Another type of catheter system is the over-the-needle system. In such a system, a catheter is placed over a rigid needle. The needle and catheter are simultaneously inserted into the patient's anatomical passageway. Thereafter, the needle is withdrawn from the interior of the catheter, leaving the catheter disposed within the patient.

A common problem associated with many over-the-needle catheters is that they tend to travel axially away from the tip of the needle and thus collapse during the insertion procedure. The patient's skin and tissue tend to resist the introduction of a catheter and push the distal tip of the catheter body backward. The catheter body thus wrinkles in an accordion or bellows-like manner over the needle as the distal end of the catheter travels backward toward the proximal end thereof while the needle is urged through the skin and tissue. This tendency of the catheter to wrinkle results from urging the catheter into the patient by applying a force to a separate needle as opposed to the catheter. Currently, virtually all over-the-needle catheters are formed of a single thermoplastic material such as polyvinylchloride (PVC), Teflon® polyurethane or the like, which provides stiff columnar strength during insertion. The catheter also remains relatively stiff when disposed within an anatomical passageway. Such stiffness traumatizes the walls of the anatomical passageway and typically requires removal of the catheter from the passageway or vessel in two days or less.

An over-the-needle catheter is described in U.S. Pat. No. 5,533,988, issued on Jul. 9, 1996 to Dickerson et al. and entitled "Over-The-Needle Catheter". The catheter includes a flexible body and a hardened tip at the distal end. The hardened tip forms an abutment at the distal end of the catheter. A rigid needle extends within the catheter during the insertion process. The rigid needle engages the abutment in an attempt to prevent the catheter body from collapsing during the insertion process. The hardened tip may comprise a metal, among other materials. Optionally, the tip may comprise a plastic material which softens upon contact with moisture or upon reaching a temperature approximately equal to the patient's body temperature.

A significant disadvantage of both the prior art through-the-needle and over-the-needle systems is that a sharpened needle must be removed once the catheter has been inserted into the patient. Removal of the sharpened needle undesirably exposes both the patient and the medical practitioner to accidental contact with the needle, a continuing problem in view of the highly contagious and/or fatal nature of such diseases as AIDS and Hepatitis A. Removal of the sharpened needle with the catheter in place also presents the problem of damage to the catheter itself.

Certain modifications have been made to minimize the possibility of accidental contact of patients or medical practitioners with the needle. One such modification is described in U.S. Pat. No. 5,683,370, issued Nov. 4, 1997 to Luther et al. entitled "Hard Tip Over-The-Needle Catheter and Method of Manufacturing the Same." The catheter assembly includes an introducing needle which includes a cylindrical protective guard or sheath which is slidably advanced over the sharp tip of the needle after the catheter is inserted and the needle is removed from the patient.

However, current devices and methods still require some action by the medical practitioner to remove and dispose of a sharpened needle immediately after inserting the catheter. The timing of this procedure presents drawbacks. Often a catheter is inserted at a moment when time is of the essence. For example, the patient may require emergency medical treatment. The risks associated with the removal of such sharp objects therefore could be minimized by waiting until the patient's treatment is concluded, a time which often involves less haste and less risk to adversely affect a patient's health.

In addition to the above-described drawbacks associated with present catheters, catheters have also exhibited a limited useful lifetime or viability. For example, present intravenous catheters typically need to be removed approximately every forty-eight hours and then a new catheter is inserted into a different area of the passageway to leave the passageway wall intact. Thus, a catheter must be replaced numerous times in even a short hospital stay by a patient which increases the risks of accidental sticks and contamination. Additional drawbacks are present as well. The removal and reinsertion of catheters increases the trauma to the patient's anatomical passageways, e.g. blood vessels. The frequent replacement of catheters during the course of a patient's treatment also increases medical costs, in terms of both time and materials. Accordingly, a catheter would ideally remain in place until the patient's need for treatment with a catheter is completed. Several factors, however, affect how long a catheter may remain viable.

The principal reason for the need to frequently remove and replace a catheter relates to the trauma it causes to the patient's anatomical passageways such as blood vessels. The trauma may be caused by movement of the patient and/or the portion of the catheter assembly located outside the patient. For example, with regard to an intravenous catheter such external movement is translated to the portion of the catheter located within the patient's vein and causes the catheter to press against the inside wall of the vein. Such pressure may lead to damage to the inner walls of the patient's vein or even internal bleeding. The flexibility of a catheter affects the degree to which it presses against the inside of the vein. Although catheters are generally flexible, they have not heretofore been flexible enough to alleviate the problem associated with a catheter pressing against the inside of a patient's anatomical passageway.

Another problem associated with catheters relates to undesirable clotting of blood sometimes associated with certain materials of construction. Depending upon the material of construction of the catheter, blood may form clots when it is drawn up into the catheter. One such material which sometimes causes blood to clot is Teflon®. Although the flow of fluids is typically from the catheter into the patient, the flow sometimes reverses. For example, when an instrument is removed from the fluid communication line connected to the catheter, it may result in a small decrease in pressure within the catheter thereby causing fluid to back up into the catheter from the patient's vascular system. When the fluid within the tip of the catheter includes blood it may sometimes clot within the Teflon® catheter. Once flow is returned to normal, the clotted blood may be introduced back into the patient's vascular system. This can lead to various problems. Because the tip of the catheter remains in contact with the blood when the catheter is disposed within a blood vessel, the material of construction of the inner portion of the catheter tip often plays a significant role in the degree of undesirable clotting.

The needle tip used in connection with the insertion of catheters, whether it be over-the-needle or through-the-needle systems, is typically formed by an oblique angle cut at the end of a hollow tube or cannula. While a needle formed in such a manner is highly effective for insertion, it can sometimes pass entirely through an anatomical passageway such as a blood vessel or can damage the opposing wall of the passageway during the insertion process. The degree to which such deleterious effects can be avoided depends almost entirely on the skill of the medical practitioner performing the insertion. Moreover, when the needle tip is to remain within the passageway for an extended period during treatment, such conventional needle tips may increase the possibility of trauma to the inside surface of the passageway depending upon the particular application. Therefore, a new catheter with a safety inserter is needed by those skilled in the art to increase safety of patients and healthcare workers alike.

SUMMARY OF THE INVENTION

The present invention provides a catheter comprising a flexible tube with a sharpened needle tip permanently secured to a distal end of the catheter to facilitate insertion of the catheter into a patient's anatomical passageway. The sharpened needle tip secured to the catheter remains within the patient's blood vessel during treatment. As a result, the invention does not require that a separate sharpened needle be inserted with the catheter and then removed immediately after the catheter is properly positioned.

Another feature of this invention is that it provides a catheter with increased flexibility to minimize trauma to the interior of an anatomical passageway such as a blood vessel, which increases the time period during which the catheter remains viable within the patient, and also increases the length of catheter which can be maintained within the anatomical passageway. The flexibility of the tube allows the needle tip to be flow directed towards the center of the vessel thereby minimizing trauma to the vessel and increasing the time period during which the catheter remains viable.

An additional advantage of the preferred embodiment of this invention is that it provides a catheter tip formed of a material which minimizes the clotting of blood which may back up into the catheter.

The preferred embodiment uses a retaining material adjacent the distal end of the flexible tube and extending around a portion of the circumference of the sharpened needle tip to secure the needle tip to the distal end of the catheter. To provide further support to the needle, one or more cavities are advantageously formed in the outer surface of the needle, which are filled with the material of the flexible tube, the retaining material, or both. Additional securement is provided by the melting and mingling of the two plastic materials comprising the flexible tube and retaining material when the needle tip is affixed to the distal end of the catheter.

A further feature of the preferred catheter assembly apparatus and method is that insertion of the catheter into a blood vessel or the like does not require a separate sharpened inserter to be used with the catheter. The catheter assembly comprises a catheter and a safety inserter. The safety inserter may be removably engaged within the catheter. Preferably, the inserter comprises a base portion and a distal end portion. The proximal end of the safety inserter is sized to accommodate a hydrophilic filter plug and/or a luer tip of a syringe. The distal end portion is sized to fit within the sharpened needle tip. The base portion is sized to fit within the flexible tube and to abut an annular shoulder formed by the proximate edge of the needle tip. Preferably, this inserter has a blunt distal end since the sharpened needle tip secured to the distal end of a flexible tube enables insertion of the catheter into the patient's anatomical passageway such as a blood vessel.

In accordance with a further aspect of the present invention, the safety inserter has a closed distal end and corresponds to the shape of the needle tip at the distal end of the catheter. Such a catheter is particularly useful as an epidural catheter or a catheter to access implanted ports wherein no flashback is required.

In accordance with a further aspect, the invention provides a needle tip and method of forming the same wherein the point of the needle tip is substantially aligned with a central axis of the lumen defined by the needle tip or cannula from which it was derived. The improved needle tip minimizes the risk of injury to walls of an anatomical passageway.

Further features and advantages of the present invention will become apparent to those of skill in the art in view of the detailed description of preferred embodiments which follow, when considered together with the attached claims.

BRIEF DESCRIPTION OF THE DRAWINGS

FIG. 1 is a perspective view of a catheter assembly of the present invention, comprising a safety inserter and a catheter.

FIG. 2 is a perspective view of a catheter of the present invention.

FIG. 3 is a cross-sectional view of the catheter.

FIG. 4 is a perspective view of an alternative embodiment of the distal end of the catheter.

FIG. 5 is an enlarged cross-sectional view of the distal end of a catheter of the present invention showing a preferred mechanism for securing the sharpened needle at the distal end of the catheter.

DETAILED DESCRIPTION OF THE PREFERRED EMBODIMENTS

Figure 6:
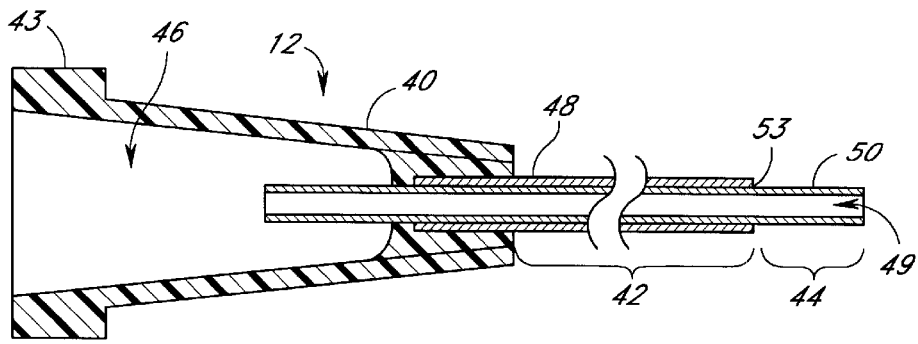
FIG. 6 is a cross-sectional view of a safety inserter of the present invention.

FIG. 1 depicts the improved catheter assembly 10 of the present invention. The catheter assembly 10 comprises a safety inserter 12 and a catheter 14.

Referring to FIGS. 2 and 3, the catheter 14 comprises a flexible tube 16 defining a lumen 18 therethrough. A sharpened needle tip 20 is secured to a distal end of the flexible tube 16. A hub 22 is formed at a proximal end of the catheter 14. The hub 22 facilitates connection of the catheter 14 with an administration line (not shown) to provide for the communication of fluids through the catheter 14, as will be easily understood by those skilled in the art.

The flexible tube 16 advantageously is preferably formed of a soft thermoplastic material. Preferably, the flexible tube 16 is formed of a material having a hardness value between 50 and 90 Shor A, more preferably between 65 and 85 Shor A, and most preferably approximately 70 Shor A. In a preferred embodiment, the flexible tube 16 is formed of polyurethane. A suitable polyurethane is sold under the tradename Carbothane™ by Thermedics Corporation of Woburn, Mass. and has a hardness value of approximately 70 Shor A.

The soft flexible tube 16 minimizes the trauma to the internal surface of the anatomical passageway into which the catheter 14 is placed. Thus, movement of the patient and/or the catheter 14 located outside the patient is not substantially translated to movement of the portion of the flexible tube 16 within the patient's anatomical passageway. When the catheter 14 is disposed within an anatomical passageway such as a blood vessel, the flexibility of the tube 16 allows the catheter 14 to be flow directed to the center of the blood vessel, the area of highest velocity flow which is sometimes referred to as the "hemodynamic center" of the vessel. The minimization of trauma to the internal surface of the blood vessel allows the catheter 14 to remain viable for longer periods than heretofore feasible. When used intravenously, the catheter 14 of the present invention may remain viable for a treatment period in excess of seven days, and preferably in excess of ten days. In some instances the catheter 14 may remain viable for two weeks or more. The increased viability of the catheter 14 has many advantages. For example, it decreases the number of times a patient will need to be "stuck" due to the removal and reinsertion of a catheter 14 during the course of treatment. In addition, it minimizes the number of times medical practitioners are exposed to sharp needles and the potential for accidental sticks. It also decreases the cost, in terms of both time and materials, associated with the use of multiple catheters during the course of treatment. The flexibility of the tube 16 also allows for an increased length of tube to be extended within the patient's anatomical passageway as the application may require.

Flexible tubes containing flexible interwoven wires in the tubular wall such as manufactured by H.V. Technologies of Trenton, Ga. are available. These tubes have the advantage of high strength, high radiopacity and high flow rates because of decreased wall thickness. Walls of only 0.003 inches are possible.

The size of the flexible tube 16 varies by application. Generally, the outside diameter of the flexible tube 16 will range from approximately 0.02 to 0.08 inches. A flexible tube 16 of a preferred embodiment for intravenous use has an outside diameter of 0.035 inches, a wall thickness of 0.005 inches, and thereby forms a lumen of 0.025 inches in diameter.

Referring to FIGS. 3, 4 and 5 a sharpened needle tip 20 is secured to a distal end of the flexible tube 16. In one aspect of the invention the sharpened needle tip 20 is formed by cutting the end off a conventional sharpened cannula. The cannula comprises an elongated tube defining a lumen and having an oblique angled cut to form its sharp end.

The needle tip 20 therefore has an inner surface 24 defining a lumen 28. The proximal end of the needle tip 20 forms a short tube 30 (FIG. 3). The distal end of the needle tip 20 has a piercing point 26.

Preferably, the sharpened needle tip 20 is formed of a metal. One suitable metal is a 300 Series stainless steel. The needle tip 20 may be a suitable length for the application at issue. Preferably, it is approximately 0.1 to 0.25 inches in length. The outside diameter of the needle tip 20 corresponds to the inside diameter of the flexible tube 16 of the catheter 14. Preferably, the diameter of the lumen 28 defined by the inner surface of the needle tip 20 is approximately 60–90% of the outside diameter so as to maintain the structural integrity of the needle tip 20 during use.

At least a portion of the proximal end of the needle tip 20 extends into the distal end 17 of the flexible tube 16. In a preferred embodiment wherein the needle tip 20 has length of 0.23 inches, approximately 0.13 inches extend within the flexible tube 16. Referring to FIG. 5, preferably the outer surface 32 of the needle tip 20 is adjacent the inner surface 34 of the flexible tube 16. The proximal edge of the needle tip 20 forms an annular shoulder 36 within the flexible tube 16. The lumen 28 of the sharpened needle tip 20 is in fluid communication with the lumen 18 defined by the flexible tube 16. Preferably, the lumen 28 of the sharpened needle tip 20 is coaxial with the lumen 18 defined by the flexible tube 16.

Referring to FIG. 3, the proximal end of the flexible tube 16 is attached to a hub assembly 22 and is in fluid communication therewith. The hub assembly 22 facilitates connection of the catheter 14 to a communication line from which fluids are administered to a patient. Any suitable hub assembly 22 may be utilized as is understood in the art.

As shown in FIG. 3, in a preferred embodiment, the catheter 14 further comprises a strain relief 38 disposed around the flexible tube 16. The strain relief 38 facilitates the attachment of the flexible tube 16 to the hub 22 and also provides additional structural integrity to the flexible tube 16. This is useful if the catheter 14 needs to clamped. For example, after the catheter 14 is inserted into a patient, a hemostasis clip may be applied to prevent the flow of fluids through the catheter 14 while an administration line is connected. By applying the clip to the outer surface of the strain relief 38, it will close the lumen 18 of the flexible tube 16 without creating the risk of damaging the flexible tube 16 which is in fluid communication with the patient's anatomical passageway. In a preferred embodiment, the flexible tube 16 and strain relief 38 are fixed within a hub 22. Alternatively, they can be fixed to an outer surface of a hub 22 or other apparatus so long as fluid communication is maintained through the catheter 14 and hub 22.

Referring to FIGS. 1 and 6, the safety inserter 12 of the catheter assembly 10 comprises a base 40, a body portion 42 and a distal portion 44. In a preferred embodiment, the base 40 facilitates handling of the catheter assembly 10 during insertion of the catheter 14 and subsequent removal of the inserter 12. The base 40 therefore preferably includes a surface 43 for gripping during the insertion and removal process. The base 40 further defines a flashback chamber 46, which can also be configured to accommodate a luer. As shown in FIG. 1, a hydrophilic plug 11 is inserted into the flashback chamber which facilitates venting of air from the flashback chamber 46 while also preventing leakage of blood or fluids therefrom. The base 40 of the inserter is adapted to engage the hub 22 of the catheter 14. In a preferred embodiment, the base 40 forms a friction fit with the hub 22.

Figure 7:
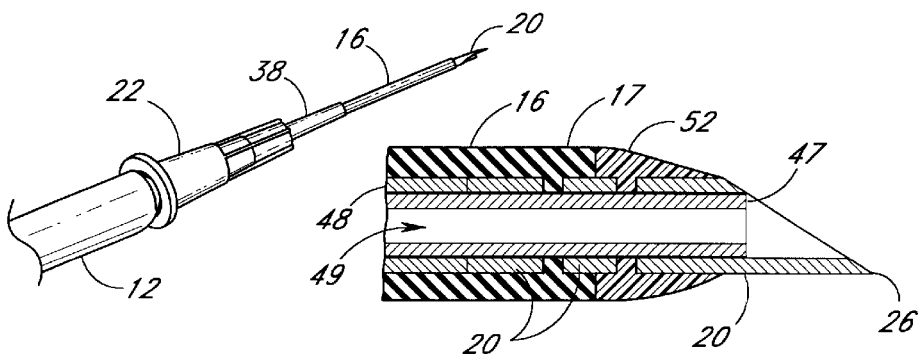
FIG. 7 is a perspective and an enlarged cross-sectional view of the distal end of the catheter assembly wherein the safety inserter is inserted into the catheter.

Referring to FIGS. 6 and 7, the body portion 42 of the safety inserter 12 is sized to fit within the lumen 18 of flexible tube 16 of the catheter 14, but not within the lumen 28 formed by the sharpened needle tip 20. The distal end portion 44 of the safety inserter 12 is sized to fit within the lumen 28 formed by the sharpened needle tip 20 of the catheter 14. The distal edge 47 of the distal end portion 44 of the inserter 12 need not be sharp, and is preferably blunt to avoid the possibility of damage to the catheter 14 or the risk of needle stick injuries.

In a preferred embodiment, the body portion 42 of the safety inserter 12 is formed by a cannula 48 having an outside diameter corresponding to the diameter of the lumen 18 defined by the flexible tube 16 of the catheter 14. A smaller cannula 50 is fixed within the larger cannula 48. The small cannula 50 extends out from a distal end of the large cannula 48 to form the distal end portion 44 of the safety inserter 12. The outside diameter of the smaller cannula 50 corresponds to the inside diameter of the sharpened needle tip 20 and the inside diameter of cannula 48. Alternatively, the safety inserter 12 may be manufactured as a unitary piece.

When the safety inserter 12 is engaged within the catheter 14, the distal edge 53 of the large cannula abuts the annular shoulder 36 formed at the proximal edge of the sharpened needle tip 20. In a preferred embodiment, the sharpened needle tip 20 is formed by cutting the sharp end off a sharpened cannula 48. The remaining cannula is then used as the large cannula 48 of the safety inserter 12. This assures that the needle tip 20 and large cannula 48 are properly sized.

The lumen 49 defined by the large and small cannulas 48, 50 may be in communication with the flashback chamber 46 of the base 40. In one embodiment, the small cannula 50 extends into the flashback chamber 46; however, the cannula 50 may terminate distal the flashback chamber 46 as will be easily understood.

The sharpened needle tip 20 may be secured to the flexible tube 16 in any suitable manner. A particularly effective means of attachment comprises the use of a radio frequency (RF) welder. Application of the RF energy heats the flexible tube 16 material of the catheter 14 and causes it to adhere to the sharpened needle tip 20. Additionally, it causes the simultaneous melting and some commingling of the two plastic materials forming the flexible tube 16 and retaining material 52 to further promote the securement of the needle tip 20.

In a preferred embodiment, the catheter 14, as shown in FIG. 5, further comprises a retaining material 52 adjacent the distal end of the flexible tube 16 and disposed around at least a portion of the outer surface of the needle tip 20. Preferably, the retaining material 52 forms an annular ring surrounding the outer circumference of the needle tip 20. A mandrel (not shown) is preferably placed within the flexible tube 16 and the needle tip 20 during the attachment process. Alternatively, a safety inserter 12 of the present invention can be used for this purpose. The retaining material 52 and a portion of the flexible tube 16 are then heated with the RF welder. Pressure may also be applied to the outer surface of the flexible tube 16 and the retaining material 52. The retaining material 52 adheres to the needle tip 20 and tube 16 during the welding process. Likewise, the tube 16 adheres to the needle tip 20 during welding.

The retaining material 52 preferably comprises a plastic having a hardness greater than the material forming the flexible tube 16. Preferably the retaining material is a polyurethane. In one preferred embodiment the retaining material is a polyurethane having a hardness value of approximately 99 Shor A. The retaining material may, of course, be of any other hardness.

In another aspect of the invention, a first set of one or more cavities 54a, b are formed in the outer surface 32 the needle tip 20. The cavities 54a, b extend from the outer surface 32 of the needle tip 20 toward the inner surface 24. Preferably, the cavities extend from the outer surface 32 to the inner surface 24 forming a hole through the outer circumference of the needle tip 20. During the attachment process, the needle tip 20 is positioned within the distal end of the flexible tube 16 with the first set of one or more cavities 54a, b located distal the end of the flexible tube 16. The retaining material 52 is formed in an annular shape around the circumference of a portion of the needle tip 20 extending beyond the flexible tube 16 and covering the holes 54a,b. A mandrel is placed within the flexible tube 16 and needle tip 20. The retaining material 52 is heated with the RF welder. In its molten state the retaining material 52 fills the first set of one or more cavities 54a, b to further secure the needle tip 20 to the flexible tube 16. In addition, the retaining material 52 adheres to the tube 16.

In another aspect of the invention, a second set of one or more cavities are formed in the outer surface 32 of the needle tip 20. Preferably, the cavities 56a, b extend from the outer surface 32 to the inner surface 24 forming a hole through the outer circumference of the needle. Alternatively, the cavities may be indentations that do not extend through the needle tip 20. During the attachment process, the needle tip 20 is positioned within the distal end of the flexible tube 16 with the first set of one or more attachment cavities 54a, b located beyond the end of the flexible tube 16, and the second set of one or more attachment cavities 56a, b located within the lumen 18 defined by flexible tube 16. The retaining material 52 is formed in an annular ring around the circumference of the needle tip 20 as described above. Another advantage of the invention is the harder (99 Shor A) material can be formed to eliminate any transition shoulder between the point of the needle tip 20 and the flexible tube 16 thereby minimizing trauma during insertion. An RF welder is applied to the retaining material 52 and flexible tube 16 as described above. The first set of one or more cavities 54a, b is filled with the retaining material 52. The material of the flexible tube 16 fills the second set of one or more cavities 56a, b.

The cavities 54, 56 can be any suitable size, depending upon the size of the needle tip 20 and the corresponding flexible tube 16. In a preferred embodiment the cavities 54, 56 form holes in the needle tip 20 having a diameter of 0.005 inches. A sufficient number of holes may be used, but not so many that would interfere with the structural integrity of the needle tip 20. In a preferred embodiment of the invention, the first and second sets of cavities 54, 56 each comprise two holes. It should be understood that the tube 16 retaining material 52 and needle tip 20 may be adhered without the use of holes or indents. Moreover, the tube 16 may be adhered to the needle tip 20 without the use of a retaining material 52 as will be understood by those skilled in the art. For example, the tube 16 may be RF bonded directly to the needle tip 20 and the distal end 17 of the tube may be sloped toward the needle tip 20 in the bonding process to eliminate a shoulder which may harm a vessel wall upon insertion of the catheter 14 in a passageway of a patient.

Of course, the needle tip 20 may be provided with external projections which communicate with indents or holes in the flexible tube 16 and/or retaining material 52 to add in securing the tip 20 to the tube 16 and/or material 52 as will be easily understood by those of skill in the art.

Figure 8:
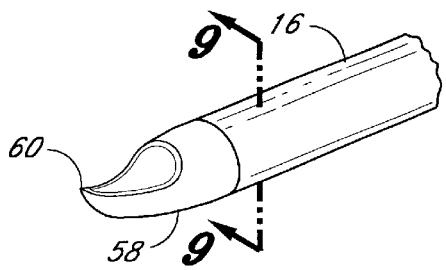
FIG. 8 is a perspective view of the improved sharpened needle tip of the present invention.
Figure 9:
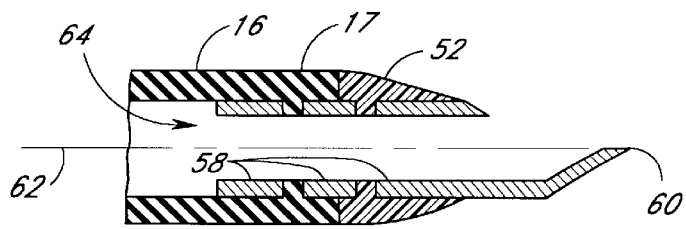
FIG. 9 is an enlarged cross-sectional view of the improved sharpened needle tip of the present invention.

FIGS. 8 and 9 illustrate another embodiment of the invention wherein an improved needle tip 58 has been adapted to minimize trauma to the interior of the anatomical passageway in which it is inserted. The conventional needle tip 20 shown, for example, in FIG. 5 has a piercing point 26 at its most distal end. The piercing point 26 is aligned with the outer surface 32 of the short tube 30 forming the proximal end of the needle. In the embodiment wherein the needle tip 20 is formed by cutting an end off a sharpened cannula, the point 26 is in a place defined by a portion of the wall of the cannula. The improved needle tip 58 of this further aspect of the invention has a piercing point 60 substantially aligned with a central axis 62 of the lumen 64. Preferably, the improved needle tip 58 is formed by bending a conventional needle tip 20 so that the piercing point 60 of the needle tip 58 is so aligned. Alternatively, the needle can be manufactured in the desired configuration. By providing the needle point 60 substantially along the central axis 62 of the lumen 64 of the needle tip 58, the risk of the needle tip 58 piercing the opposing wall of a passageway or vessel of a patient is significantly reduced, both during the insertion process and while the catheter 14 is disposed within a patient's anatomical passageway. In practice, a healthcare worker sometimes inserts a standard needle tip 20 too far, so that it enters the vessel and then pierces the opposing wall of the vessel. Upon withdrawal of the needle tip, internal bleeding occurs. By placing the point 60 along the central axis 62, the risk of piercing the opposite vessel wall is significantly reduced because the catheter is typically inserted into the vessel at an acute angle to the longitudinal axis of the vessel, as will be easily understood by those of skill in the art. Similarly, the point 60 of needle tip 58 will naturally be less likely to contact the inside wall of an anatomical passageway in which it is disposed thereby reducing the risk of trauma to the patient.

Having thus described the construction of certain preferred embodiments of the apparatus of the present invention and the associated method of making the same, a preferred treatment method utilizing the apparatus of the invention is described. The safety inserter 12 is initially placed within the catheter 14. The distal end portion 44 of the safety inserter 12 extends within the lumen 28 defined by the needle (FIG. 7). The distal edge 47 of the distal end portion 44 extends sufficiently far into the needle tip 20 to provide support during insertion but not so far that the blunt end 47 of the inserter will interfere with the piercing point 26 of the needle tip 20. The body portion 42 of the inserter extends within the flexible tube 16 of the catheter 14. The distal edge 53 of the outer cannula 48 forming the base portion 42 preferably abuts the proximal edge 36 of the needle tip 20 to allow the practitioner to urge the catheter 14 into a patient's anatomical passageway by applying force to the inserter 12, which is translated to the needle tip 20. In one preferred application the catheter 14 is urged into a patient's vein to provide intravenous treatment to the patient.

Once the catheter 14 is properly placed within the patient's anatomical passageway, a homeostasis clip or suitable device is applied to close the flexible tube 16. Preferably the clip is applied to the strain relief 38. The catheter 14 is held in place while the inserter 12 is removed. The blunt inserter 12 is eventually discarded. The hub 22 of the catheter 14 may then be connected to a fluid communication line such as a standard administration set. The catheter 14, including the sharpened needle tip 20, remains disposed within the patient's anatomical passageway. Fluid communication is established through the catheter 14 wherein fluids are infused into or withdrawn from the patient by removal of the clip. Preferably, the catheter 14 remains in place during the entire period in which the patient is treated with a catheter 14. Thereafter, the catheter 14 is removed. Because the sharpened needle tip 20 is disposed at the end of a flexible tube 16 as opposed to a rigid cannula as in prior art inserters, the risk of accidental sticks is minimized. Furthermore, because the catheter 14 is often removed at the conclusion of treatment, there is typically a lesser degree of haste involved, thereby allowing the medical practitioner to more easily exercise the proper degree of care in removing and discarding the needle tip 20.

Figure 10:
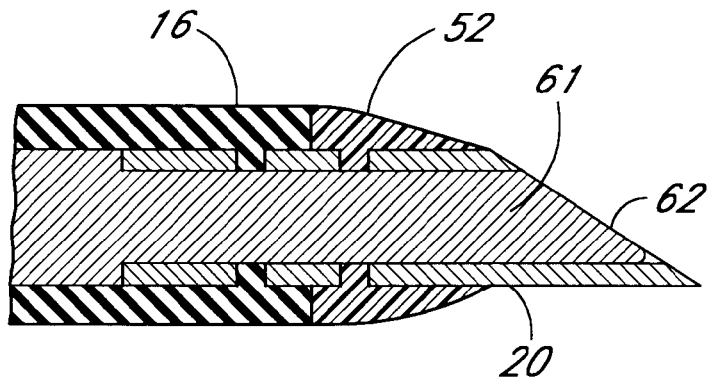
FIG. 10 is an enlarged cross-sectional view of the distal end of the catheter assembly wherein the safety inserter has a closed distal end.
Figure 11:
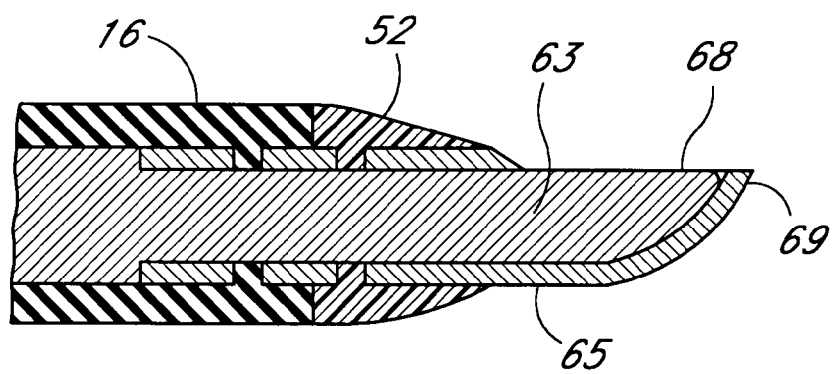
FIG. 11 is an enlarged cross-sectional view of the distal end of the catheter assembly wherein the safety inserter has a closed distal end corresponding to the internal configuration of an epidural needle tip.

FIGS. 10 and 11 illustrate further aspects of the invention, which are particularly useful for applications which do not require a flashback. These include epidural catheters and catheters used to access implanted ports such as described in U.S. Pat. No. 5,403,283 issued on Apr. 4, 1995 to Luther and entitled "Percutaneous Port Catheter Assembly and Method of Use". The inserters 61 and 63 do not include a lumen through their length and preferably are closed at their distal end. This aspect of the invention is particularly suitable for epidural catheters since the catheter is ideally formed so as not to introduce tissue into the epidural space. An open lumen at the distal end of the catheter 14 may cause tissue to be carried into the epidural space during the insertion process.

Referring to FIG. 10, the inserter 61 is sized to fit within the lumen 18 defined by the flexible tube 16 and the lumen 28 formed by the sharpened needle tip 20. The distal end 62 of the inserter 61 preferably corresponds roughly to the shape of the needle tip 20. The distal end 62 of the inserter is preferably blunt to prevent the inserter 61 from piercing or penetrating the skin of a person. The end of the inserter may be sand-blasted to provide the dull or blunted distal end 62.

FIG. 11 illustrates an embodiment that is particularly suitable for use in epidural applications. The needle tip 65 has a distal end 69 configured in the Toughy or Hustead configuration of conventional epidural needle points. The insert 63 corresponds roughly to the shape of the needle tip 65, and is preferably dulled or blunted at its distal end 68.

Although the present invention has been described in terms of certain preferred embodiments, other embodiments of the invention will become apparent to those of skill in the art in view of the disclosure herein. Accordingly, the scope of the present invention is not intended to be limited by the foregoing, but rather by reference to the attached claims.

What is claimed is:

1. An improved catheter assembly (i) which does not require that a separate sharpened needle be inserted with the catheter and then removed immediately after the catheter is in place in an anatomical passageway such as a blood vessel, (ii) which resists clotting, and (iii) which minimizes the trauma to such anatomical passageway so that the catheter may remain in place for an extended period of time, said catheter assembly comprising:

an elongated flexible tube, a needle tip for enabling insertion of said tube into said anatomical passageway, said needle tip fixedly secured to the distal end of said flexible tube such that said needle tip is located within said anatomical passageway during use of said catheter to introduce fluids into said anatomical passageway, said tube having sufficient flexibility so that said needle tip is allowed to be flow directed toward the center of said anatomical passageway when said tube is located therewithin, and a safety inserter comprising first and second concentric cannulas, said second cannula disposed within said first cannula and extending from a distal end of said first cannula, said second cannula sized to be removably engaged within said needle tip and said first cannula sized to be removably engaged within said flexible tube, said inserter removably placed within said flexible tube and said needle tip during insertion of said flexible tube into the anatomical passageway, said inserter having sufficient rigidity so that said flexible tube can be initially positioned within said anatomical passageway without collapsing during the insertion procedure.

2. The catheter assembly of claim 1, wherein said needle tip has a piercing point at its distal end, and said piercing point is aligned with a central axis of the lumen defined by said needle tip.

3. The catheter of claim 1, wherein said flexible tube comprises a soft material having a hardness value of between 50 and 90 Shor A.

4. The catheter of claim 1, wherein said flexible tube comprises a soft material having a hardness value of approximately 70 Shor A.

5. The catheter of claim 1, wherein said flexible tube comprises polyurethane.

6. The catheter of claim 1, wherein said catheter further comprises a retaining material adjacent the distal end of said flexible tube and disposed around a portion of the outer surface of said needle tip.

7. The catheter of claim 6, wherein said retaining material comprises a hard plastic.

8. The catheter of claim 1, wherein said needle tip has an outer surface and an inner surface defining the lumen, said outer surface defines a first cavity extending from said outer surface toward said inner surface, and said retaining material extends into said first cavity to assist in holding said needle tip in place.

9. The catheter of claim 8, wherein said outer surface of said needle tip defines a second cavity extending from said outer surface toward said inner surface and said flexible tube extends into said second cavity to further assist in holding said needle tip in place.

10. The catheter of claim 8, wherein said first cavity extends from said outer surface to said inner surface of said needle to form a hole therethrough.

11. The catheter of claim 8, wherein said second cavity extends from said outer surface to said inner surface of said needle to form a hole therethrough.

12. A catheter assembly for inserting a catheter into an anatomical passageway, said catheter assembly comprising:

an elongated flexible tube having a distal end;

a needle tip defining a lumen secured to the distal end of said flexible tube, said needle tip having a sharp distal end to enable insertion of said flexible tube into said passageway and a proximal end extending into the distal end of said flexible tube; and an inserter removably placed within said flexible tube and said needle tip, said inserter having a base portion and a distal end portion, the distal end portion sized to fit within the lumen in said needle tip, said base portion comprising an outer cannula and said distal end portion comprising an inner cannula extending from a distal end of said outer cannula.

13. The catheter of claim 12, wherein said distal end portion of said inserter has a blunt tip.

* * * * *